(12) United States Patent
Venturino et al.

(10) Patent No.: US 6,630,088 B1
(45) Date of Patent: Oct. 7, 2003

(54) FORMING MEDIA WITH ENHANCED AIR FLOW PROPERTIES

(75) Inventors: Michael Barth Venturino, Appleton, WI (US); Daniel Mark Duhm, Greenville, WI (US); Steven John Shimon, Sherwood, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 450 days.

(21) Appl. No.: 09/694,374

(22) Filed: Oct. 23, 2000

(51) Int. Cl.<sup>7</sup> ................................................. A61F 13/15
(52) U.S. Cl. ...................... 264/121; 264/517; 264/518; 425/80.1; 425/83.1
(58) Field of Search ................................ 264/517, 518, 264/121; 425/80.1, 81.1, 82.1, 83.1

(56) References Cited

U.S. PATENT DOCUMENTS

| | | | |
|---|---|---|---|
| 3,518,726 A | 7/1970 | Banks | 19/144.5 |
| 4,140,508 A * | 2/1979 | Pelagio | 65/476 |
| 4,592,708 A | 6/1986 | Feist et al. | 425/80.1 |
| 4,666,647 A | 5/1987 | Enloe et al. | 264/121 |
| 4,674,966 A | 6/1987 | Johnson et al. | 425/82.1 |
| 4,761,258 A | 8/1988 | Enloe | 264/518 |
| 5,466,409 A | 11/1995 | Partridge et al. | 264/165 |

FOREIGN PATENT DOCUMENTS

EP        0338111        10/1989

* cited by examiner

Primary Examiner—Mary Lynn Theisen (57) ABSTRACT

A forming receptacle and method for receiving particulate material thereon, and thereby fabricating particulate congregates for use as absorbent cores in personal care absorbent articles is disclosed. The forming receptacle can comprise sheet material defining bottom and side walls of the receptacle. The bottom and side wall have first and second major surfaces and a thickness. The forming receptacle also comprises an array of apertures connecting first and second major surfaces, and further comprises a matrix of sheet material between apertures defining outer perimeters of respective apertures. Respective aperture walls taper from the first major surface toward the second major surface. Aperture walls of adjacent apertures intersect the second major surface without intersecting each other. The array of apertures can be arranged in a series of parallel rows wherein spacing between apertures is substantially constant from row to row. The rows can be displaced laterally such that adjacent apertures in adjacent rows define angles with respect to an imaginary line parallel to the rows. The apertures, measured at a smallest cross-section of opening, can define a composite open area representing at least about 35 percent of the combined areas of the bottom and side walls. Some embodiments introduce a forming drum comprising a plurality of forming receptacles designed and configured to form particulate congregates. The forming drum can comprise mounting structure for mounting the forming drum about an axis of rotation, and a forming receptacle repository extending about a circumference of the forming drum and supported from the mounting structure.

53 Claims, 7 Drawing Sheets

FORMING MEDIA WITH ENHANCED AIR FLOW PROPERTIES

BACKGROUND OF THE INVENTION

The present invention relates to forming receptacles and methods for receiving particulate material thereon, and thereby fabricating particulate congregates for use as absorbent cores in personal care absorbent articles. More particularly, one of the contemplated applications for the present invention is in a forming drum comprising a plurality of forming receptacles designed and configured to form particulate congregates for use as absorbent cores in personal care absorbent articles.

Current forming media used to form particulate congregates for use as absorbent cores in personal care absorbent articles comprises a perforated plate or woven screen having a 20×20 or 30×30 thread weave per inch wherein the holes are arranged in a rectangular pattern. While the geometry of the known art is functional, such geometry does have significant drawbacks.

The holes arranged in a rectangular pattern, typical of woven screens and perforated plates used in the art, does not facilitate optimum formation of personal care absorbent articles because the fraction of the open area represented by the holes in the screen or plate, is so low as to impede desired rates of air flow through the screen or plate. There is a need for a more porous media.

The inventors herein have discovered that rectangular arrangement of the forming media holes is less efficient than improved media of the invention.

The hole size of the conventional screens is nearly twice the size of an average particle of super-absorbent material (SAM) as may typically be used in fabricating personal care absorbent articles. SAM lost by passing through the e.g. screen or perforated plate results in significant in-process loss that must be compensated for by overfeeding the SAM system.

The conventional hole arrangement is also subject to plugging, caused by a single particle, or multiple particles, of SAM getting lodged into a single perforation or hole. Compressed air is periodically used to dislodge as many of the plugged holes as possible. Over the course of a few weeks, screens become significantly plugged, the machine must be shut down, and the screens must be removed and steam cleaned, thus significantly hindering the quality and rate of operation for production of significant elements of personal care absorbent articles.

Screen plugging is also a common occurrence with woven wire screens. The weaving of the wires creates "pinch points" that trap fibers. The pinch points also become more severe as a flat screen is distorted into the three-dimensional shape of a pocketed forming surface. The pinch points tend to become an even greater problem as the what-was square or rectangular shaped openings of the screen become distorted into a rhombus or diamond-shape through the process of forming a receptacle. This distortion, or pinching off, of the holes can create a significant amount of pinch points and can be severe enough that localized areas of the screen have significantly poor porosity. Thus, different areas of the screen have different porosities, resulting in different air flow rates through the screen at the different areas. Different air flow rates define respective different levels of accumulation of absorbent core material, e.g. fiber and SAM, at the respective different areas, whereby the interval uniformity, or thickness, within a given absorbent core so produced may be less than desired.

The problem for the present invention is thus to provide forming media, as well as methods, for receiving particulate material thereon, and thereby fabricating particulate congregates for use as absorbent cores in personal care absorbent articles, whereby the holes in the forming media are not arranged in a rectangular array, and whereby the configurations of individual ones of the holes in the forming media discourage plugging of the forming media.

It is an object of this invention to create a geometric mismatch between SAM particles and respective forming media holes, by employing hole configurations which reduce the frequency of SAM particles getting lodged in the holes and thus reducing or closing off air flow through the respective holes.

It is another object of this invention to create forming media, void of pinch points and burrs which catch SAM particles and promote plugging, by employing forming media which are manufactured to be absent such pinch points and burrs.

It is yet another object of this invention to improve on the current linear arrangement of holes in forming media, by employing a hole arrangement which promotes improved airflow.

It is still another object of this invention to improve effectiveness of airflow throughout the forming area, by employing forming media having optimum porosity.

SUMMARY OF THE DISCLOSURE

In a first family of embodiments, the invention comprises a forming receptacle. The forming receptacle is adapted and configured to receive particulate material thereon, including super-absorbent particles, for thereby fabricating particulate congregates for use as absorbent cores in personal care absorbent articles. The forming receptacle comprises sheet material defining a bottom wall of the receptacle, and a side wall of the receptacle extending upwardly from the bottom wall thereby to define a particulate-receiving cavity in the receptacle. The bottom wall and the side wall have, in combination, a first major surface disposed toward the cavity, an opposing second major surface disposed away from the cavity, and a thickness between the first and second major surfaces. The forming receptacle also comprises an array of apertures extending through the bottom wall, and optionally through the side wall, and connecting the first and second major surfaces, and further comprises a matrix of the sheet material between respective ones of the apertures and defining outer perimeters of respective ones of the apertures.

In some embodiments, the bottom wall and the side wall, in conjunction, comprise a particulate receiving cavity having a depth of at least about 0.001 inch to about 2.00 inches. Yet in other embodiments, bottom wall and the side wall, in conjunction, comprise a particulate receiving cavity having a depth of about 0.00 inch.

In some embodiments, the apertures comprise aperture walls extending from the first major surface to the second major surface, the respective aperture walls tapering generally outwardly from central axes of the respective apertures, and from the first major surface toward the second major surface.

In some embodiments, the aperture walls define cross-sectional areas of such apertures along the thickness of the sheet material, including a first locus defining a smallest cross-sectional area, and a second locus defining a relatively larger cross-sectional area displaced from the smallest cross-sectional area and disposed, from the first locus, toward the second major surface of the sheet material. The smallest cross-sectional area can be displaced from and between both of the first and second surfaces.

In preferred embodiments, the apertures can define cross-sectional areas proximate the first and second surfaces, the cross-sectional area proximate the second surface being greater than the cross-sectional area proximate the first surface.

In some embodiments, the apertures comprise aperture walls extending generally perpendicular to the first surface from loci adjacent the first surface to interior loci between the first surface and the second surface, and tapering generally outwardly from the interior loci to the second major surface, whereby open areas defined by the respective apertures at the second major surface are greater than open areas defined by respective ones of such apertures at the first major surface.

In some embodiments, the aperture walls taper inwardly from the first major surface and toward the second major surface, to a throat zone, and taper outwardly from the throat zone to the second major surface, such that the throat zone defines an opening smaller in cross-section than corresponding openings defined by the respective aperture at either of the first or second major surfaces.

In some embodiments, a respective aperture defines an opening at the first major surface, the opening having an open area corresponding to the area of a circle having a diameter of at least about 0.009 inch, up to about 0.040 inch, preferably at least about 0.010 inch, up to about 0.025 inch, more preferably at least about 0.011 inch, up to about 0.015 inch.

In some embodiments, the matrix of sheet material at the first major surface generally has a minimum projected width between respective ones of the apertures of about 0.003 inch to about 0.015 inch, preferably about 0.005 inch to about 0.009 inch.

In preferred embodiments, aperture walls of adjacent ones of the apertures intersect the second major surface without intersecting each other, wherein such aperture walls of adjacent first and second ones of the apertures define nominal distances therebetween without intersecting each other.

In preferred embodiments, the matrix of sheet material at the second major surface generally has a minimum width between respective ones of the apertures of about 0.0007 inch up to about 0.004 inch, preferably about 0.0007 inch up to about 0.003 inch, more preferably about 0.001 inch up to about 0.002 inch.

In preferred embodiments, the array of apertures is arranged in a series of parallel rows of apertures, wherein spacing between apertures in a given row is substantially constant from row to row, and wherein the rows are displaced laterally with respect to each other such that adjacent apertures in adjacent rows define angles of about 50 degrees to about 90 degrees, in some more preferable embodiments about 50 degrees to about 70 degrees, yet in other more preferable embodiments, about 80 degrees to about 90 degrees, with respect to an imaginary line parallel to the rows. Yet in some embodiments. the array of apertures is arranged sporadically, wherein spacing and orientation between apertures in a given row is substantially variable.

In highly preferred embodiments, the apertures, measured at a smallest cross-section of opening defined by each such aperture, in combination, define a composite open area representing at least about 35 percent, preferably greater than 40 percent, of the combined areas of the bottom wall and the side wall.

Thickness of the sheet material is preferably about 0.003 inch to about 0.030 inch, and more preferably about 0.005 inch to about 0.015 inch. Length of the receptacle is preferably about 10 inches to about 30 inches, more preferably about 12 inches to about 24 inches. Structures of the apertures can reflect photochemical machining.

Some embodiments comprise forming drums designed and configured to form, in a continuous process, particulate congregates for use as absorbent cores in personal care absorbent articles. Such forming drums can comprise mounting structure for mounting the forming drum about an axis of rotation, and forming receptacle repositories extending about at least a portion of a circumference of the forming drum and supported from the mounting structure. The forming receptacle repositories include ones of forming receptacles mounted about the circumference of the drum. The forming receptacles are effective to receive and accumulate thereon elongate fibers, and particles of super-absorbent material, thereby to form such congregates. Yet other embodiments comprise forming drums which can comprise mounting structure for mounting the forming drum about an axis of rotation, and a forming receptacle, the forming receptacle being uniform and continuous, and extending about substantially an entire circumference of the forming drum and supported from the mounting structure.

In a second family of embodiments, the forming receptacle comprises a substrate defining a bottom wall of the receptacle, and a side wall of the receptacle extending upwardly from the bottom wall thereby to define a particulate-receiving cavity in the receptacle. The bottom wall and the side wall, in combination, comprise elements defining a first major side disposed toward the cavity, an opposing second major side disposed away from the cavity, and a thickness between the first and second major sides. An array of apertures extends through the bottom wall, and connects the first and second major sides. Aperture walls define cross-sectional areas of such apertures along the thickness of the substrate, including a locus defining a smallest cross-sectional area, and a locus defining a relatively larger cross-sectional area displaced from the smallest cross-sectional area and disposed toward the second major side of the substrate.

In some embodiments, the forming receptacle further comprises a matrix of the substrate between respective ones of the apertures, and defining outer perimeters of respective ones of the apertures, wherein the aperture walls extend from the first major side to the second major side, and wherein respective said aperture walls taper generally outwardly between the first major side and the second major side.

In preferred embodiments, the apertures, measured at a smallest cross-section of opening defined by each such aperture, in combination, define a composite open area representing at least about 35 percent, preferably, greater than 40 percent, of the combined areas of the bottom wall and the side wall.

In a third family of embodiments, the invention comprehends a method for forming a congregate of particulate material for use as an absorbent core in an absorbent article, wherein the particulate material comprises generally particles, optionally spherically-shaped particles, of super-absorbent material. The method comprises conveying the particulate material in a gaseous carrier toward a forming receptacle. The forming receptacle comprises sheet material defining a bottom wall of the receptacle. The sheet material also defines a side wall of the receptacle extending upwardly from the bottom wall. The bottom wall and the side wall, in combination, define a particulate-receiving cavity in the receptacle. The bottom wall and the side wall have, in combination, a first major surface disposed toward the cavity, an opposing second major surface disposed away from the cavity, and a thickness between the first and second major surfaces. An array of apertures extend through the bottom wall and define passage ways between the first and second major surfaces. The passage ways are defined by aperture walls which taper generally outwardly from central axes of the respective passage ways, and from proximate the first major surface toward the second major surface. The passage ways tend to generally progressively expand in cross-sectional area as one progresses toward the second major surface, and projected areas of the particles of the super-absorbent material are generally larger than projected areas of the apertures. The method further comprises receiving and collecting particles of the particulate material in the cavity and thereby forming the congregate while generally not conveying particles of the super-absorbent material into the passage ways. Undersize particles of super-absorbent material which do enter respective ones of the passage ways tend to pass entirely through the passage ways and not become lodged in such passage ways because of being released to pass through such passage ways, by the generally progressively expanding cross-sections of such passage ways along the direction of travel of such particles.

In some embodiments, the projected area of a respective such aperture is defined by a relatively more constrictive throat zone of the respective passage way, the throat zone being disposed closer to the first major surface than to the second major surface.

A projection of such throat zone is typically no more than 25 percent, preferably no more than 15 percent, smaller in cross-sectional area than a projection of the respective aperture at the first surface. In some embodiments, a projection of the throat zone is substantially the same size in cross-sectional area as a projection of the respective aperture at the first surface.

In preferred embodiments, the method comprises receiving and collecting the particles of a such forming receptacle wherein the particles of super-absorbent material are generally oblong-shaped, having a length-to-width ratio of no more than 4/1.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components.

DETAILED DESCRIPTION OF THE ILLUSTRATED EMBODIMENTS

Figure 1:
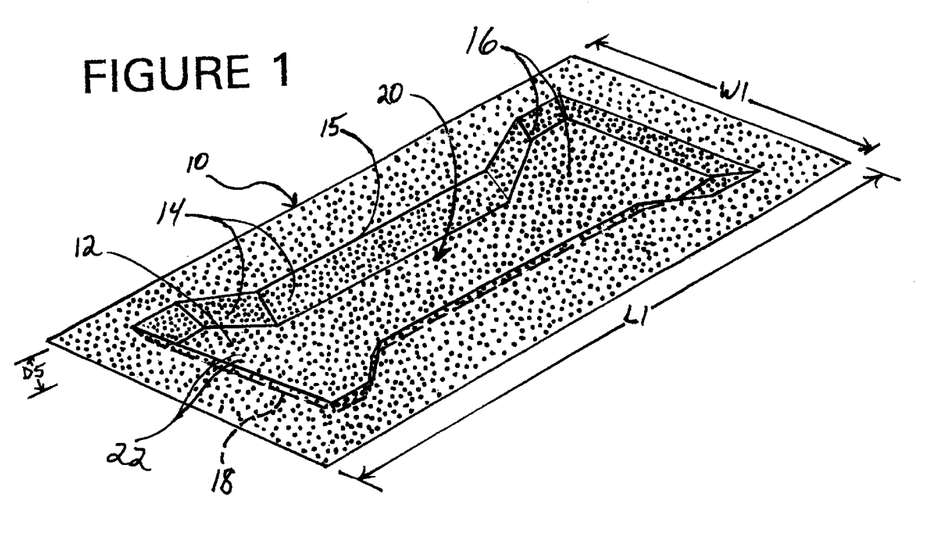
FIG. 1 shows a representative pictorial view of a receptacle of the invention.

FIG. 1 shows a forming receptacle 10 comprising a bottom wall 12 of receptacle 10, and side walls 14 of receptacle 10 extending upwardly from the bottom wall to a top edge 15 thereof. As illustrated, bottom wall 12 has a generally flat surface which meets side walls 14 of receptacle 10, side walls 14 extending upwardly to top edges 15 of side walls 14. Thus, bottom wall 12 in conjunction with side walls 14 define a particulate-receiving cavity 20 in the receptacle. Bottom wall 12 and side walls 14 have, in combination, a first major side or surface 16 disposed toward cavity 20, an opposing second major side or surface 18 disposed away from, cavity 20. An array of apertures 22 extend through receptacle 10 and connect the first and second major surfaces.

While the receptacle illustrated in FIG. 1 shows side walls 14 disposed in an angular relationship with bottom wall 12, the invention contemplates various embodiments of forming receptacles having bottom and side walls meeting in singular arcuate relationships, as well as in multiple arcuate relationships. An arcuate meeting relationship between the bottom and side wall can comprise ones of inflections as well as a plurality of effective radii defining the curvature of the arcuate meeting relationship. Similarly, while bottom wall 12 and side walls 14 of receptacle 10 are illustrated in FIG. 1 as having generally flat surfaces, some embodiments comprise one or both bottom wall 12 and side walls 14 having angled, curved, and/or arcuate surfaces.

The forming receptacle comprises a length "L1", a width "W1", a depth "D5", and a thickness. The length of the receptacle can be about 10 inches to about 30 inches, and preferably, about 12 inches to about 24 inches. The length and width of the receptacle can depend upon the size of the e.g. absorbent articles into which respective absorbent cores are to be incorporated. Alternatively, the length and width of the receptacle depend upon the desired absorptive capabilities of the absorbent core portion of such corresponding absorbent article. Some embodiments contemplate a receptacle having one or both a length and width being greater or smaller than the dimensions of the desired absorbent core, e.g. as in continuous, uninterrupted production of absorbent core material which can be segmented later.

In some embodiments, particulate-receiving cavity 20 extends across substantially the entirety of one or both the length and width of forming receptacle 10. In other embodiments, particulate-receiving cavity 20 extends across a portion of one or both the length and width of forming receptacle 10. Additionally, while most embodiments reflect a depth D5 of at least about 0.001 inch to about 2.00 inches, some embodiments contemplate a bottom wall and side walls which, in conjunction, comprise a particulate receiving cavity having a depth D5 of down to about 0.00 inch. In all embodiments, the depth of the forming receptacle is generally dependent upon the desired absorptive capabilities of the resultant absorbent core portion of such corresponding absorbent article.

The thickness of the apertured sheet material of forming receptacle 10 can be about 0.003 inch to about 0.030 inch, and preferably, about 0.005 inch to about 0.015 inch. Forming receptacle 20 preferably comprises stainless steel, but can also comprise a variety of materials including, but not limited to, metals such as nickel, aluminum, tungsten, titanium, and copper. The materials listed are preferred because the materials are formable, economical, and also non-toxic. Other materials, especially metals, which are formable, as well as economical and non-toxic are contemplated as forming receptacle materials. Other materials and substrates capable being formed and comprising tapered holes such as ceramics and plastics are also contemplated.

Figure 2:
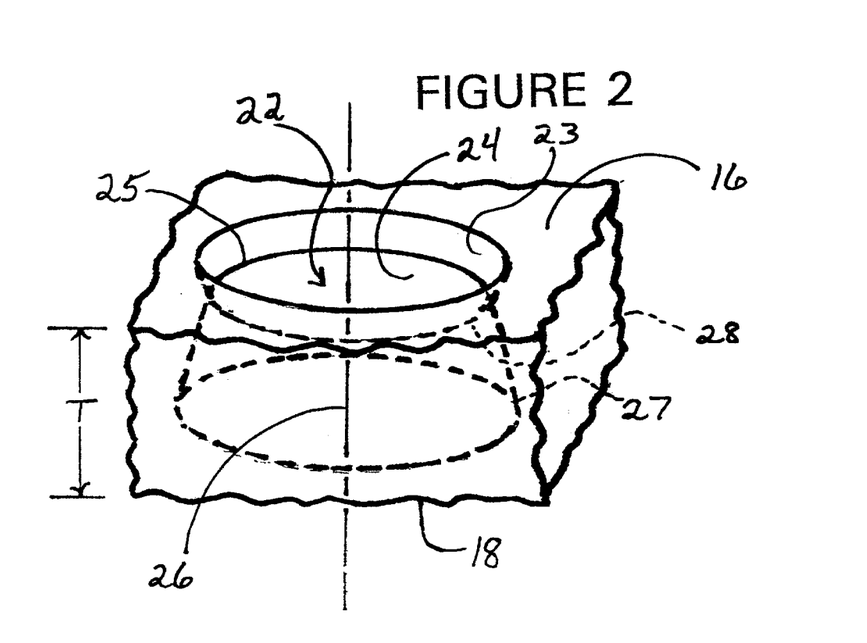
FIG. 2 shows an enlarged representative portion, in pictorial view, of an aperture, surrounded by matrix defining the aperture.

FIG. 2 shows an enlarged example one embodiment of an aperture 22 of the forming receptacle illustrated in FIG. 1. As illustrated in FIG. 2, apertures 22 generally comprise aperture walls 24 extending from first major surface 16 to second major surface 18. As illustrated in the embodiment in FIG. 2, the respective aperture walls 24 taper generally outwardly away from a central axis 26 of respective aperture 24, and generally from first major surface 16 toward second major surface 18.

Thickness "T" of the material represents the distance between top surface 16 and bottom surface 18. The thickness of the material can be about 0.003 inch to about 0.030 inch, and preferably, about 0.005 inch to about 0.015 inch.

Aperture walls define cross-sectional areas of such apertures along the thickness of the substrate or sheet material, and include a first locus 25 defining a smallest cross-sectional area, and second loci defining a relatively larger cross-sectional area displaced from the smallest cross-sectional area and disposed, from the first locus, toward second major surface 18 of the substrate or sheet material. The portion of aperture wall 24 disposed between first locus 25 and surface 16 defines an upper section 23 of aperture wall 24. Similarly, the portion of aperture wall 24 disposed between first locus 25 and surface 18 defines a lower section 27 of aperture wall 24. In the illustrated embodiment, the smallest cross-sectional area is displaced from and between both of the first and second surfaces in throat zone 28. In preferred embodiments, the apertures define cross-sectional areas proximate the first and second surfaces in which the cross-sectional area proximate second surface 18 is greater than the cross-sectional area proximate first surface 16.

Figure 3A:
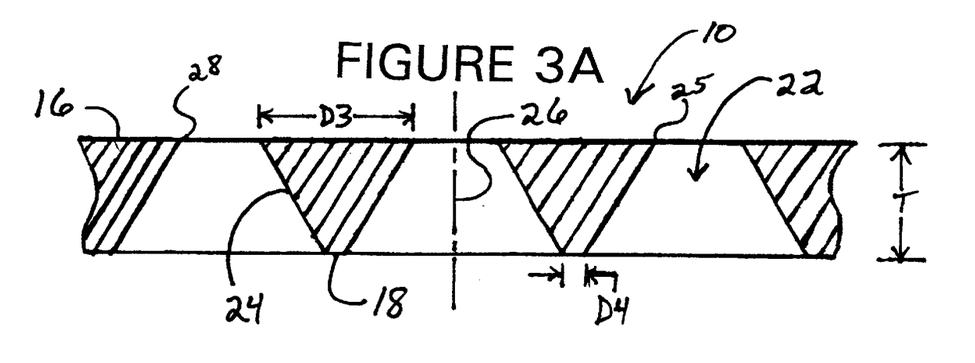
FIGS. 3A, 3B, and 3C show representative cross-sectional elevation views of certain ones of the embodiments of apertures useful in the invention.
Figure 3B:
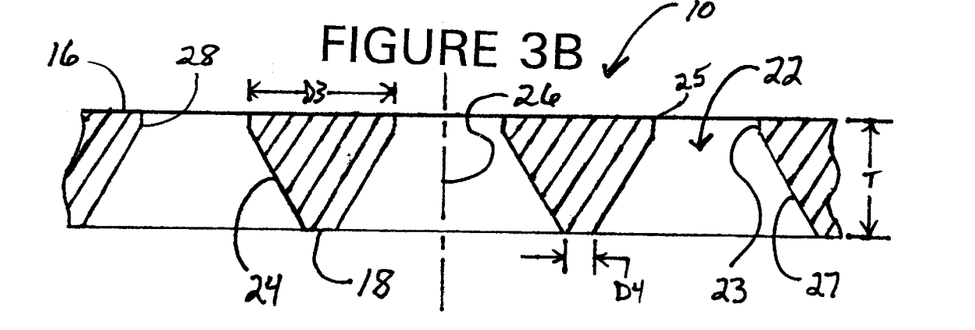
Figure 3C:
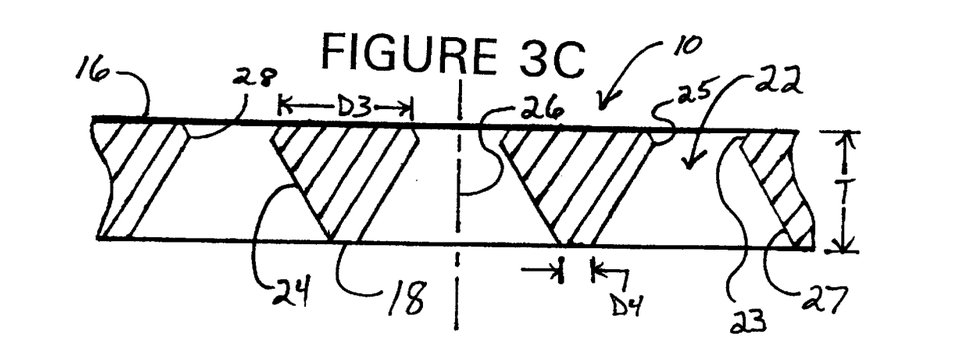

FIGS. 3A, 3B, and 3C show enlarged cross-sectional views of three illustrative embodiments of forming receptacle 10. As in FIGS. 1 and 2, thickness "T" of the material represents the distance between top surface 16 and bottom surface 18. A central aperture axis generally passes through the center of each aperture.

FIG. 3A illustrates apertures 22 comprising aperture walls 24 which extend from loci 25 or throats of smallest projected cross-section 28 at and/or adjacent first surface 16 and taper generally outwardly from the inner loci to second major surface 18. The open areas defined by the respective apertures at second major surface 18 are greater than open areas defined by respective ones of such apertures 22 at first major surface 16.

FIG. 3B illustrates apertures 22 comprising aperture walls 24 which extend generally perpendicular to first surface 16 from loci 25 adjacent first surface 16 to interior loci between first surface 16 and second surface 18, thus to define throats of smallest projected cross-sectional area 28. The interior loci are preferably closer to top surface 16 than bottom surface 18. Walls 24 then taper generally outwardly from the interior loci to second major surface 18. An upper section 23 of aperture wall 24 is defined by the portion of aperture wall 24 between throat area 28 and surface 16; similarly, a lower section 27 of aperture wall 24 is defined by the portion of aperture wall 24 between throat area 28 and surface 18. The open areas defined by respective apertures 22 at second major surface 18 are greater in cross-section than open areas defined by respective ones of such apertures 22 at first major surface 16.

FIG. 3C illustrates in cross-section a series of apertures 22 corresponding to aperture 22 as shown in FIG. 2. The apertures comprise aperture walls 24 which taper inwardly from first major surface 16 and toward second major surface 18, to an interior locus illustrated as throat zone 28. Walls 24 taper thence outwardly from throat zone 28 to second major surface 18, such that throat zone 28 defines a projected opening generally equal to or smaller in cross-sectional area than corresponding openings defined by the respective aperture at either of the first or second major surfaces. An upper section 23 of aperture wall 24 is defined by the portion of aperture wall 24 between throat area 28 and surface 16; similarly, a lower section 27 of aperture wall 24 is defined by the portion of aperture wall 24 between throat area 28 and surface 18. In some embodiments, a projection of throat zone 28 is no more than 25 percent smaller in cross-sectional area than a projection of respective aperture 22 at first surface 16. In other embodiments, a projection of throat zone 28 is no more than 15 percent smaller in cross-sectional area than a projection of respective aperture 22 at first surface 16. An aperture comprising a cross-section at surface 16 which is more than 25 percent greater in cross-sectional area than the projection of throat zones can result in creating an upper section of aperture wall 24 that is large enough to cradle and lodge particles of super-absorbent material in the aperture. In the embodiment illustrated in FIG. 3B, a projection of throat zone 28 is substantially the same size in cross-sectional area as a projection of respective aperture 22 at first surface 16.

A respective aperture 22 defines an opening at first major surface 16. The opening generally has an open area corresponding to the area of a circle having a diameter of at least about 0.009 inch, up to about 0.040 inch, preferably, at least about 0.010 inch, up to about 0.025 inch, and more preferably, at least about 0.011 inch, up to about 0.015 inch.

In some embodiments of the forming receptacle, the relationship shown between respective ones of aperture walls and surface 16 is not angular, but curved, wherein the curvature can comprise one or more effective radii.

In the embodiments illustrated in FIGS. 3A, 3B, and 3C, the matrix of sheet material at first major surface 16 generally has a minimum projected width between respective ones of the apertures "D3" of about 0.003 inch to about 0.015 inch, and preferably, about 0.005 inch to about 0.009 inch.

In order to take advantage of the full thickness "T", aperture walls 24 of adjacent ones of the apertures 22 preferably intersect second major surface 18 in very close proximity to each other without intersecting each other, thereby defining nominal distances "D4" between the respective apertures at surface 18. Preferably, the matrix of sheet material at second major surface 18 generally has a minimum width between respective ones of the apertures "D4" of about 0.0007 inch up to about 0.004 inch, preferably, about 0.0007 inch up to about 0.003 inch, and more preferably, about 0.001 inch up to about 0.002 inch.

Apertures 24 can be formed in a sheet material precursor of forming receptacle 10 by a chemical etching process, such that structures of the apertures reflect photochemical machining, such as, e.g. a photo etch process or micro-etch™ process. In a photochemical machining process, photo tooling is typically created to correspond to desired size of openings of a resultant forming receptacle precursor. Next, a substrate or sheet material to be machined is coated with a photosensitive resist. One or both sides of the substrate or sheet material can be coated with the photosensitive resist. One or both sides of the coated substrate or sheet material are then exposed with a negative image of a desired forming receptacle precursor and developed. The substrate or sheet material is then chemically processed. Each side or surface of the substrate or sheet material is treated with the chemical process. The chemical process removes unprotected portions of the substrate or sheet material, thereby creating apertures, yet does not affect the portions coated with photosensitive resist, thereby forming the array of apertures illustrated e.g. in FIG. 1, in a forming receptacle precursor. The longer each side is treated with the chemical process, the more of the substrate or sheet material is removed from that respective side or surface.

Separately treating each side of the substrate or sheet material allows for a variety aperture angles and orientations, and positionings of throat portion 28. After apertures 22 are formed, the substrate or sheet material is formed into a forming receptacle as in FIG. 1, capable of collecting congregates of particulate material. As a result of using an photochemical machining process to form apertures 22, the major planar surfaces 16, 18 of the forming receptacle are free of burrs, crevices and rough edges, with corresponding reduction in tendency for entrapping particles or bacteria, thus reducing tendency for contamination related to such entrapments.

In some contemplated embodiments, apertures on respective forming receptacles do not have to comprise the same size or same shape as other apertures of the respective forming receptacle. Similarly, some embodiments contemplate an arrays of apertures which do not comprise uniform configurations or arrangements throughout the forming receptacle.

Figure 4:
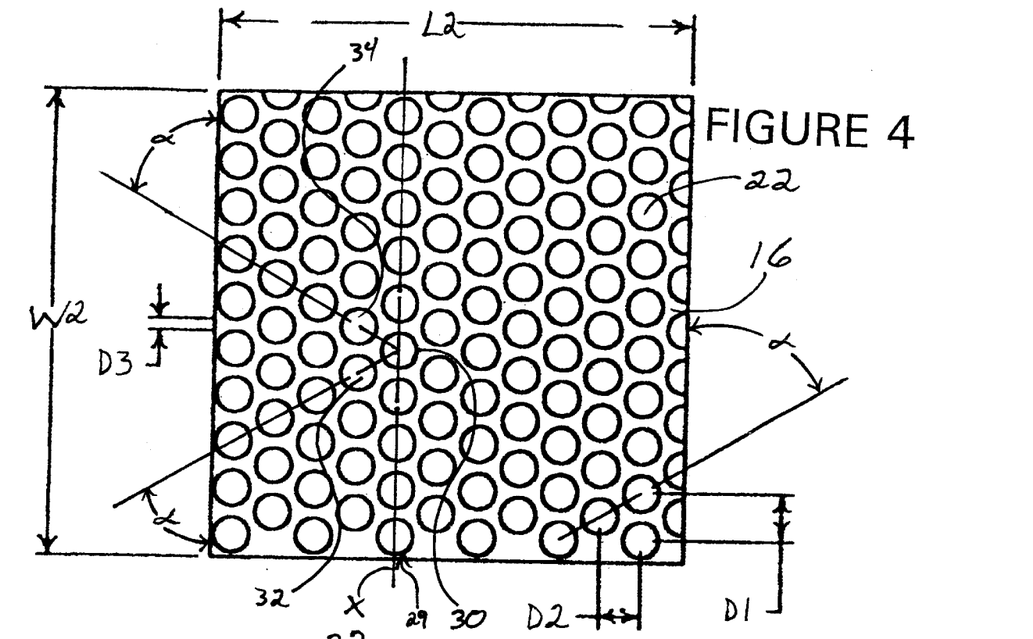
FIG. 4 shows a representative plan view of a preferred embodiment of the sheet material illustrating spacial relationships among apertures and the surrounding matrix of sheet material.

FIG. 4 shows plan view of the substrate at top surface 16 of a preferred embodiment demonstrating the spacial relationship between apertures 22 and the surrounding matrix of sheet material. While FIG. 4 shows an illustration of top surface 16 of embodiments shown in FIGS. 3A and 3B, a plan view of top surface 16 of the embodiment shown in FIG. 3C would illustrate another concentric ring representing the tapered throat region of the apertures inside that of the circular opening formed by the intersection of the aperture walls and top surface 16.

The section of sheet material shown in FIG. 4 has an exemplary length "L2" and an exemplary width "W2". Length "L2" and width "W2" are shown for illustrative purposes only, and should not be construed as limiting. The matrix of substrate or sheet material between respective ones of the apertures defines outer perimeters of respective ones of the apertures. A respective aperture 22 defines an opening at first major surface 16, the opening having an open area corresponding to the area of a circle having a diameter of at least about 0.009 inch, up to about 0.040 inch, preferably, at least about 0.010 inch, up to about 0.025 inch, and more preferably, at least about 0.011 inch, up to about 0.015 inch. The matrix of sheet material at first major surface 16 generally has a minimum projected width "D3" between respective ones of the apertures of about 0.003 inch to about 0.015 inch, and preferably about 0.005 inch to about 0.009 inch. It should be noted that "D3", as measured from projected area, is the measurement from throat-to-throat.

The array of apertures shown in the preferred embodiment illustrated in FIG. 4 is arranged in a series of parallel rows of apertures, wherein spacing between apertures in a given row is substantially constant from row to row. A row is defined as any series of apertures intersected by a straight line where the straight line intersects the center-point of origin of any two adjacent apertures. In the illustrated embodiment, the distance "D1" between center points of adjacent apertures of a given row can be about 0.010 inch to about 0.050 inch, and preferably about 0.012 inch to about 0.020 inch. In the illustrated embodiment, the distance between center points of adjacent apertures in adjacent rows "D2" can be about 0.008 inch to about 0.045 inch, and preferably, 0.010 inch to about 0.018 inch.

In some embodiments, the rows of apertures are displaced laterally with respect to each other such that adjacent apertures in adjacent rows define angles "$\alpha$" of about 50 degrees to about 90 degrees with respect to an imaginary line extending parallel to the rows. In some preferred embodiments, the rows of apertures are displaced laterally with respect to each other such that adjacent apertures in adjacent rows define angles "$\alpha$" of about 80 degrees to about 90 degrees with respect to an imaginary line extending parallel to the rows. In yet other preferred embodiments, the rows of apertures are displaced laterally with respect to each other such that adjacent apertures in adjacent rows define angles "$\alpha$" of about 50 degrees to about 70 degrees with respect to an imaginary line extending parallel to the rows. Such line can be represented by e.g. line "X" illustrated in FIG. 4. The corresponding angle "$\alpha$" in FIG. 4 ins illustrated at 60 degrees.

Imaginary reference line "X" indicates a reference row 29 including reference aperture 30, reference line "X" intersecting the radial origin of reference aperture 30. Reference aperture 30 juxtaposes a first adjacent aperture 32 and a second adjacent aperture 34. Angle "$\alpha$" can be defined by the angular relationship between reference line 30 and a line passing from the radial origin of reference aperture 30 intersecting the radial origin of either first adjacent aperture 32 or second adjacent aperture 34.

The apertures in the substrate, measured at smallest cross-sections of the openings defined by such apertures, in combination, define a composite open area fraction of the apertured substrate representing at least about 35 percent, and preferably, greater than 40 percent, of the area of the substrate, and preferably corresponding open area of the bottom wall and the side wall.

In an exemplary calculation drawn from FIGS. 3A or 3B, aperture diameter at surface 16 is about 0.012 inch, "D3" is about 0.005 inch, "D2" is about 0.014 inch, "D1" is about 0.016 inch, length "L2" of the portion of the receptacle illustrated is about 0.160 inch, and width "W2" of the portion of the receptacle illustrated is about 0.170 inches. Dividing the sum of the circular areas, and portions thereof, defined by the apertures confined in the rectangular area, defined by the product of "L2" and "W2", by the product of "L2" and "W2" results in a fraction of 0.0127 inch open area/0.0272 inch total area, or a quotient of 0.467, or 46.7 percent open area for the exemplary dimensions. Similar calculations can be done for embodiments of FIG. 3C, considering that the open area is more restricted at the throat zone than at either surface 16 or 18, whereby open area is calculated based on the open area at the throat zone, which is disposed between surfaces 16 and 18. Such open area as to all embodiments is readily defined in terms of the projected open area of the respective apertures.

Figure 5A:
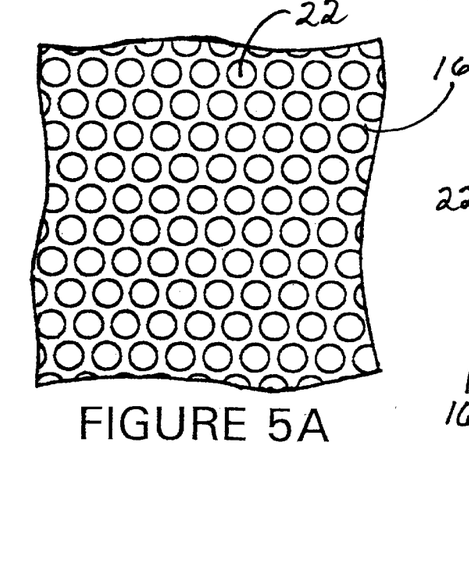
FIGS. 5A, 5B, and 5C show representative plan views of the top surface of three preferred embodiments of the invention.
Figure 5B:
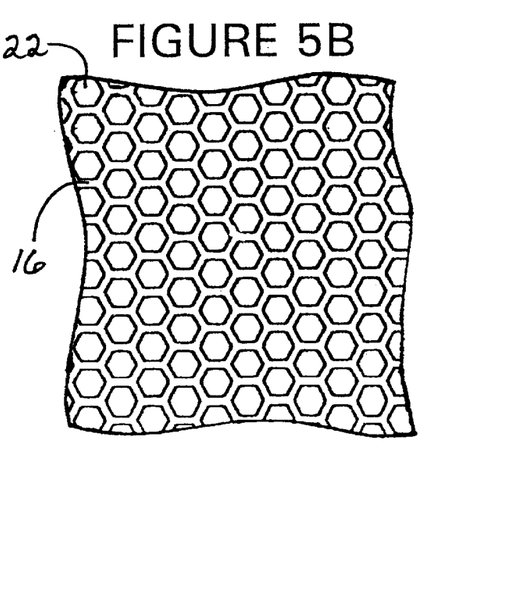
Figure 5C:
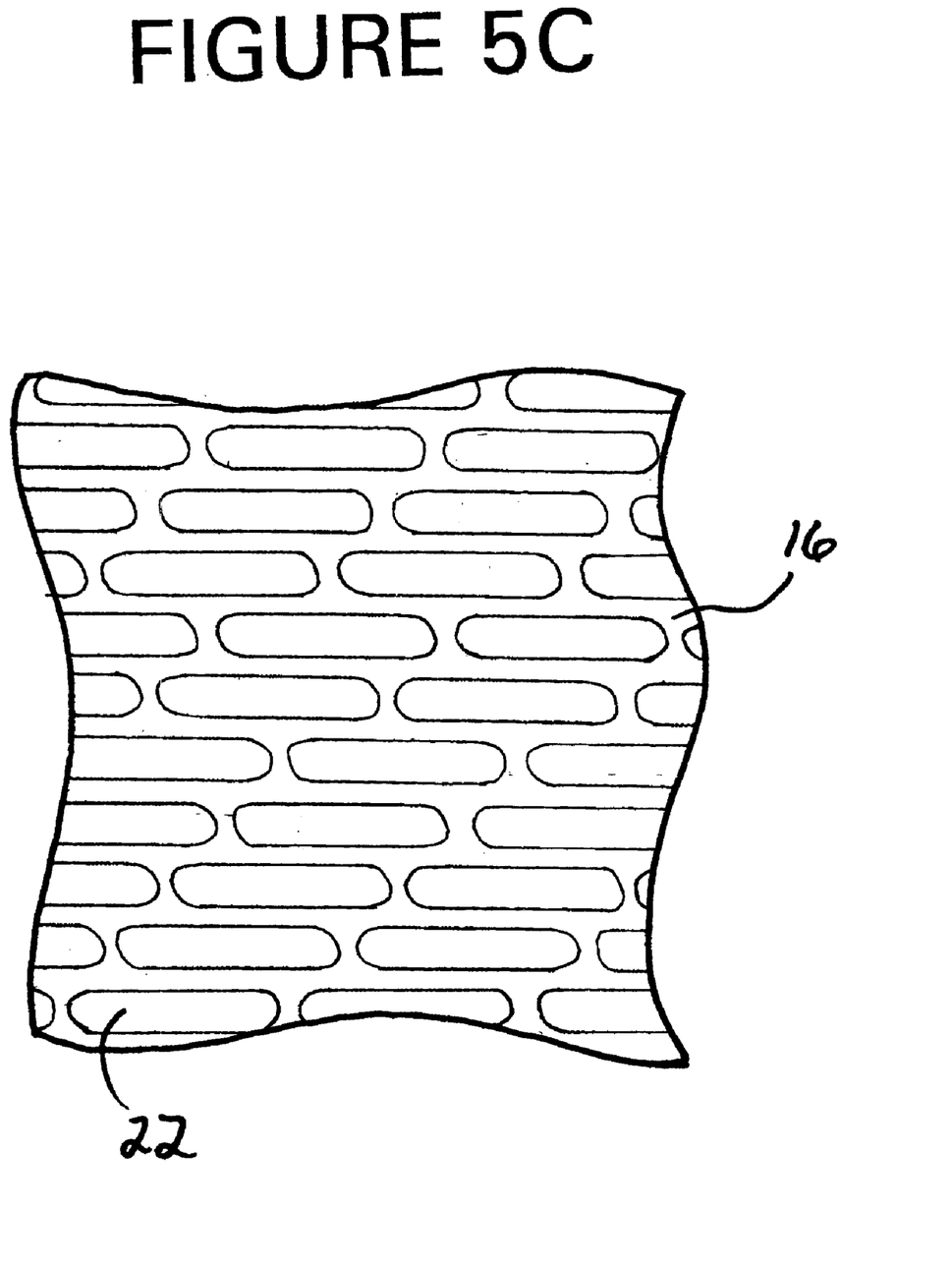

FIGS. 5A, 5B, and 5C show plan views of the top surface of three preferred embodiments of the invention. The apertures in the substrate, measured at smallest cross-sections of the openings defined by such apertures, in combination, define a composite open area fraction of the apertured substrate representing at least about 35 percent, and preferably, greater than 40 percent, of the area of the substrate, and preferably corresponding open area of the bottom wall and the side wall. The designed percentage of open area is a balance between structural integrity of the matrix of sheet material comprising the receptacle and porosity of the receptacle providing greater air flow. Thus, using the preferred configurations of the portions of the receptacles in FIGS. 5A, 5B, and 5C, maximum air flow can be achieved without sacrificing strength of the receptacle, since the amount of sheet material between apertures can still provide structural integrity throughout the receptacle.

While apertures having circular, hexagonal, and slit-shaped cross-sections are illustrated, the invention contemplates apertures of other cross-sectional configurations including, but not limited to, triangular, quadrilateral, pentagonal, septagonal, octagonal, nonagonal, decagonal, ovoid, elliptical, and arcuate shapes.

Figure 6:
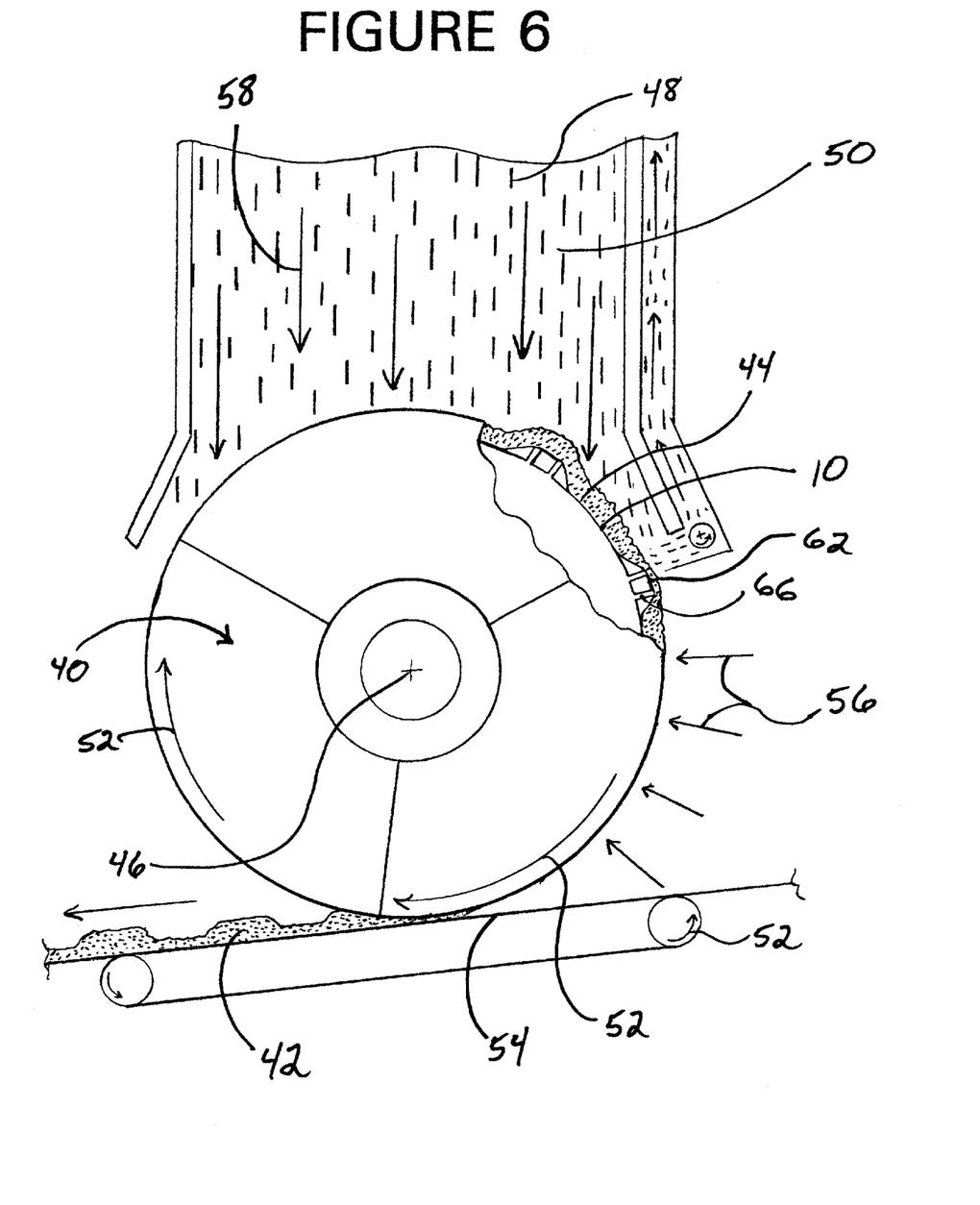
FIG. 6 shows a representative elevation side view of an application of the invention on a first embodiment of a forming drum used for collecting and congregating absorbent cores for absorbent personal care articles.
Figure 6A:
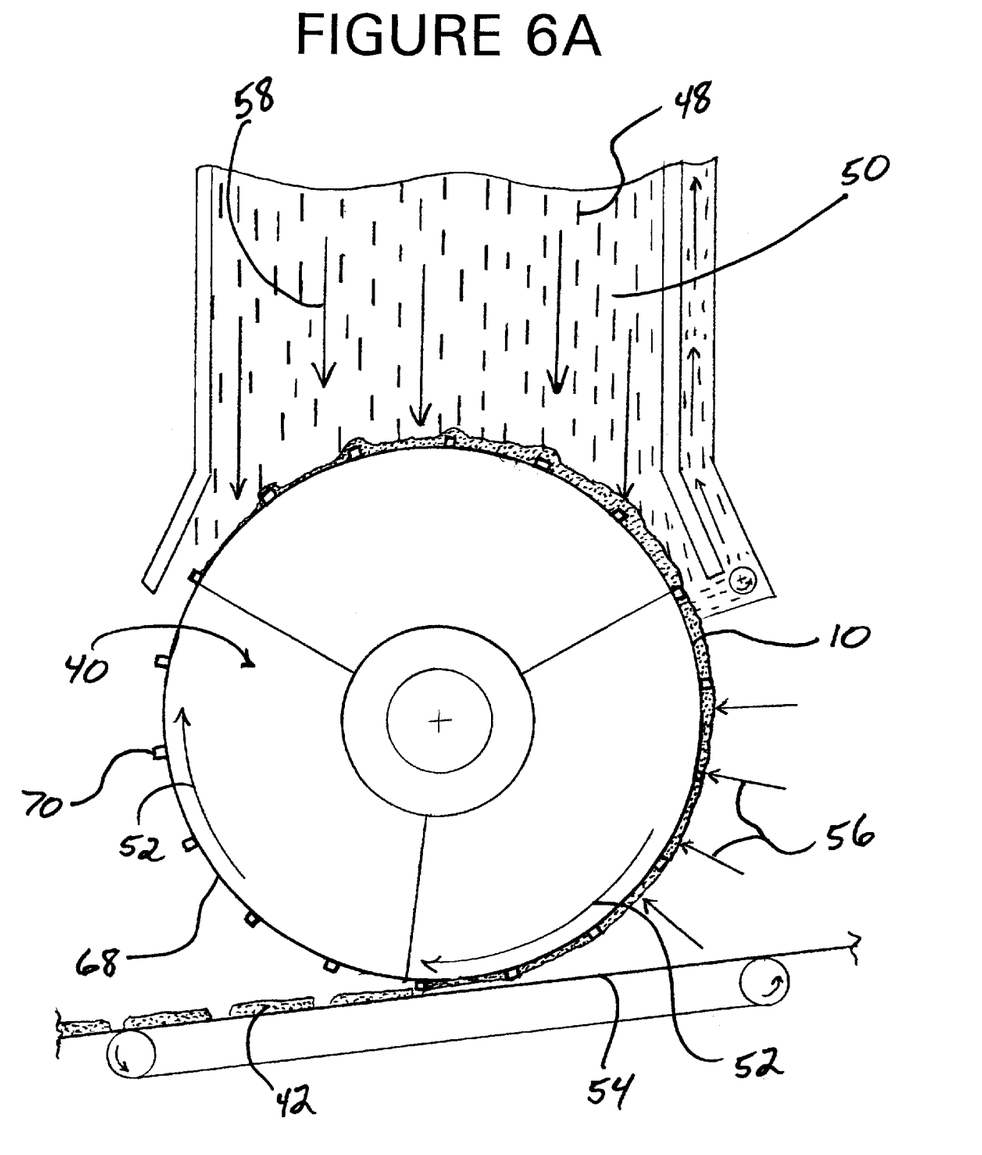
FIG. 6A shows a representative elevation side view of an application of the invention on a second embodiment of a forming drum used for collecting and congregating absorbent cores for absorbent personal care articles.

Referring to FIGS. 6 and 6A, FIG. 6 shows a side elevated view of an application of receptacles 10 on a forming drum 40 used for collecting and fabricating absorbent cores for use in absorbent personal care articles. Forming receptacles 10 are disposed about at or near outer circumference of forming drum 40 in forming receptacle repository 44. Forming drum 40 can be designed and configured to form, in one or both a continuous and an intermittent process, individual or continuous particulate congregates 42 for use as absorbent cores in personal care absorbent articles. Forming drum 40 comprises a support frame or other mounting structure (not shown) for mounting forming drum 40 from a support surface and about an axis of rotation 46. Ones of forming receptacle repositories 44 extend about at or near at least a portion of circumference of forming drum 40 and is supported from the mounting structure. Ones of forming receptacle repositories 44 each include a forming receptacle mounted at or near a portion of the circumference of the drum. The forming receptacles tend to be effective in receiving and accumulating thereon one or both elongate fibers and particles of super-absorbent material, thereby to form particulate congregates 42.

Forming chamber 50, a closed conveyance device, conveys particulate material comprising super-absorbent material and elongate fibers in harmony with direction of high air-flow, generally created by, and not limited to, vacuum forces, and shown by arrows 58. The high air-flow forces then direct particulate materials toward forming receptacles 10, disposed about at or near the circumference of forming drum 40, to congregate on first major surface 16 (FIG. 7) of respective forming receptacles 10. As forming wheel 40 rotates with respect to the direction of rotation shown at arrow 52, particulate congregates 42 are held to first major surface 16 (FIG. 7) of respective forming receptacles 10 via low air-flow forces, generally created by, and not limited to, vacuum forces, and shown by arrows 56. High air-flow forces 58 are of a greater magnitude of force than low air-flow forces 56, and include the amount of force necessary to promote the urging of super-absorbent particles and elongate fibers toward first major surface 16 (FIG. 7) of respective forming receptacles 10. Conversely, low air-flow forces 56 are of a lesser magnitude of force than high air-flow forces 58, and include the amount of force necessary to hold the particulate congregates on first major surface 16 (FIG. 7) of respective forming receptacles 10, thereby overcoming the forces of one or both gravity and centrifugal force. Particulate congregates 42 are released from forming wheel 40 as particulate congregates 42 pass beyond areas of low air-flow forces 56 at the bottom of wheel 40 adjacent the locus where the respective congregates are transferred to pick-up belt 54.

Absorbent cores of absorbent personal care articles such as the cores to be made using receptacles 10 preferably comprise a mixture 48 of super-absorbent hydrogel-forming material and elongate fibers of wood pulp in the form of fluff. Elongate fibers can include, and are not limited to, both softwood and hardwood fibers, as well as vessel elements, ranging in size from about 10 microns in diameter to about 70 microns in diameter. The elongate fibers can be up to about 5 millimeters long, preferably 1 to 3 millimeters in length. In place of the wood pulp fluff, one can use synthetic, polymeric, meltblown fibers or a combination of meltblown fibers and natural fibers.

Particles of super-absorbent material are generally spherically-shaped, or oblong-shaped, having a length-to-width ratio of no more than about 4/1. The high-absorbency material can be selected from natural, synthetic and modified natural polymers and materials. The high absorbency materials can be inorganic materials, such as silica gels, or organic compounds, such as cross-linked polymers. The high absorbency materials refer to any structure or composition, along with associated processes, which renders normally water-soluble materials substantially water insoluble but swellable, whereby absorbent properties are available but the swelled material is substantially immobile after absorbing water-based liquids. Such super-absorbent material can be fabricated by creating e.g. physical entanglement, crystalline domains, covalent bonds, ionic complexes and associations, hydrophilic associations such as hydrogen bonding, and hydrophobic associations or Van der Waals forces.

A forming receptacle can be fashioned in a variety of shapes to allow the resultant absorbent core to have any of a number of shapes. For example, forming receptacles can be fashioned to present absorbent cores that are rectangular, hour-glass-shaped, I-shaped, or T-shaped. Most absorbent cores are preferably narrower in a crotch portion than in a rear or front portion, especially where the crotch portion of the absorbent article is narrower than the rear portion or the front portion.

Forming receptacle 10 is affixed to forming drum 40 by support structures 66. Forming receptacles can be affixed to support structures 66 of forming drum 40 through a variety of mechanisms including, but not limited to, welding, clamping, screws, bolts, and adhesive. Support structures 66 can comprise any material, preferably stainless steel, aluminum, or steel, providing ample support to secure and position receptacles 10 on forming drum 40. Some embodiments comprise alternative support structures which also allow air flow between adjacent forming receptacles. In some embodiments, support structures 66 demonstrate a porous bridge 62 which enables air flow therethrough caused by air-flow forces, other embodiments are contemplated wherein corresponding bridge structures do not allow airflow between adjacent forming receptacles. Bridge 62 can comprise a variety of nonporous and porous materials, including forming receptacle precursor material.

In some contemplated embodiments, outer circumferential surface 68 (FIG. 6A) of forming drum 40 can comprise a length of apertured forming receptacle precursor material, comprising forming receptacles constructed into the precursor material, and such precursor material wrapped about all or portions of the circumference of forming drum 40. FIG. 6A illustrates a second embodiment of the invention showing forming drum 40 comprising a continuous layer forming receptacle 10 which substantially covers outer circumferential surface 68. While forming receptacle 10 generally retains a similar contour as outer circumferential surface 68, particulate congregates can be continuous, or segregated into individual units using optional dividing members 70. Dividing members 70 can be adhered to either the continuous layer forming receptacle or directly to outer circumferential surface 68 of forming drum 40 using a variety of mechanisms including, but not limited to, welding, clamping, screws, bolts, and adhesive.

Figure 7:
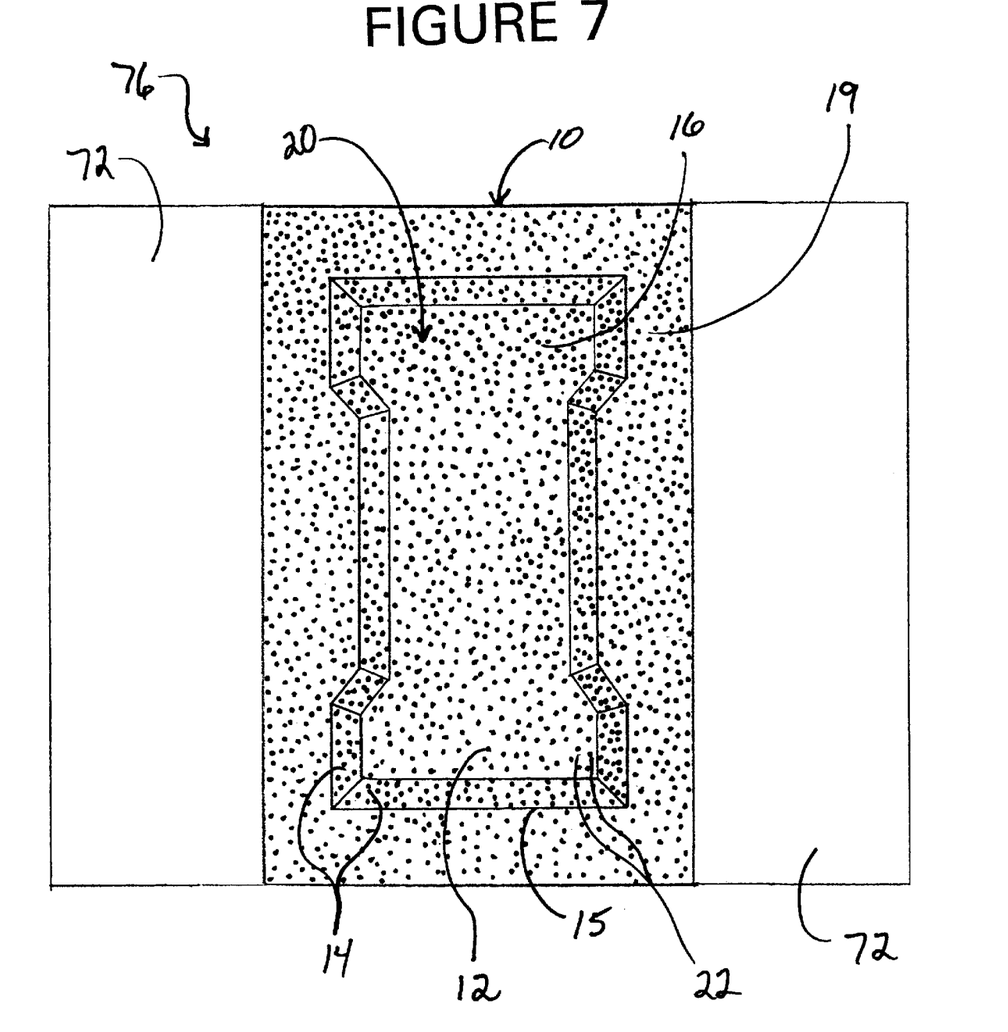
FIG. 7 shows an enlarged top view of a forming receptacle and companion attachment apparatus, which can be attached to a forming drum.

FIG. 7 illustrates an enlarged top view of an embodiment of forming receptacle. 10 and companion attachment apparatus 72, which can be attached to a forming drum. Also illustrated in FIG. 1, forming receptacle 10 comprises a bottom wall 12, and side walls 14, which meet the bottom wall and extend up to top edge 15 thereof. While bottom wall 12 and side walls 14 are illustrated as having generally flat surfaces, embodiments comprising arcuate, angled, and rounded walls are also contemplated. Bottom wall 12 in conjunction with side walls 14 define a particulate-receiving cavity 20 in the receptacle. Bottom wall 12 and side walls 14 have, in combination, a first major side or surface 16 disposed toward cavity 20, and an opposing second major side or surface (FIG. 1) disposed away from cavity 20. An array of apertures 22 extend through receptacle 10 and connect the first and second major surfaces.

Forming receptacle 10 can be adhered to a forming drum through a variety of mechanisms. FIG. 7 illustrates a preferred embodiment for attachment to a forming drum. Attachment plates 72 can be adhered to forming receptacle 10 at an attachment portion 19 of forming receptacle 10 located between top edge 15 and attachment plate 72. The attachment portion of the forming receptacle can be altered by means such as cutting, bending, drilling, or punching, so as to provide a compatible area of attachment with respective attachment plate(s). Attachment plate 72 is affixed to attachment portion 19 of forming receptacle 10 by way of a variety of affixing mechanisms including, but not limited to, welds, clamps, screws, bolts, and adhesives. Forming receptacle 10 and affixed attachment plate 72 define a forming plate 76. Forming plate 76 then can be affixed to a forming drum, like e.g. the embodiment of FIG. 6,through a variety of affixing mechanisms including, but not limited to, welds, clamps, screws, bolts, and adhesives.

While forming receptacle 10 of FIG. 7 illustrates an attachment portion 19 which comprises apertures, other embodiments are contemplated having less or substantially no apertures, with relationship to side walls 14 and bottom wall 12, in attachment portion 19 of forming receptacle 10.

The invention functions to receive and collect particles of the particulate material at first major surface 16 of forming receptacle 10 and thereby to form the congregate while generally not conveying particles of the super-absorbent material into the passage ways defining apertures of each respective forming receptacle. Undersize particles of super-absorbent material which do enter respective ones of the passage ways tend to pass entirely through the passage ways and not become lodged in such passage ways because of being released to pass through such passage ways. Namely, generally progressively expanding cross-sections of such passage ways along the direction of travel of such particles from top surface 16 to bottom surface 18, tends to alleviate risk of clogging apertures in a respective forming receptacle. The invention also contemplates coating or treating forming receptacle material with one or more "non-stick" treatments, such as Teflon® or electropolishing, thereby providing an additional hindrance to particles lodging in the apertures.

While choosing to not be bound by theory, the inventors herein contemplate that the reduced tendency for lodging is a result of the combination of smaller aperture cross-section, the reduced portion of thickness "T" represented between entrance surface 16, and throat portion 28, and the expanding cross-section of the aperture between throat region 29 and exit surface 18. In addition, in embodiments such as FIG. 3C, throat region 28 can function as a cutting or abrading edge to cut or abrade SAM particles which are marginally too small to pass through the respective aperture, whereby throat 28 causes size reduction in some SAM particles that would otherwise not pass, allowing them to pass.

As used herein, "entrance surface" refers to surface 16 and further refers to the surface from which SAM and fiber particles enter apertures 22. Similarly, "exit surface" refers to surface 18 and further refers to the surface from which SAM and fiber particles exit apertures 22.

Below is a distribution table (TABLE 1) of two examples of typical super-absorbent particle size distribution per US Sieve.

TABLE 1

| Sieve Size | Example 1 | Example 2 |
| --- | --- | --- |
| 20 | 0.4% | 0.3% |
| 30 | 20.0% | 22.0% |
| 50 | 53.0% | 55.0% |
| 170 | 25.0% | 21.0% |
| 325 | 0.9% | 2.0% |
| >325 | 0.2% | 0.1% |

In both examples of particulate super-absorbent material, the overwhelming majority of particles of super-absorbent material tend to settle on the 30 mesh, 50 mesh and 170 mesh sieves. A standard 30 mesh sieve comprises nominal openings of approximately 0.033 inch, a standard 50 mesh sieve comprises nominal openings of approximately 0.012 inch, and a standard 170 mesh sieve comprises nominal openings of approximately 0.004 inch. Therefore, the distance between distal walls of a respective aperture in a receptacle of the invention will tend to be less than the size of the average particles of super-absorbent material tested.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:
1. A forming receptacle adapted and configured to receive particulate material thereon, including super-absorbent particles, for thereby fabricating particulate congregates for use as absorbent cores in personal care absorbent articles, said forming receptacle comprising sheet material which defines a particulate receiving cavity in said receptacle, said sheet material having a first major surface disposed toward the cavity, an opposing second major surface disposed away from the cavity, and a thickness between the first and second major surfaces, and an array of apertures extending through at least a portion of said sheet material, and connecting said first and second major surfaces, and further comprising a matrix of said sheet material between respective ones of the apertures and defining outer perimeters of respective ones of the apertures, wherein the apertures comprise aperture walls extending from the first major surface to the second major surface, and wherein respective said aperture walls taper generally outwardly from central axes of the respective apertures.

2. A forming receptacle as in claim 1, wherein respective said aperture wails taper generally from the first major surface toward the second major surface.

3. A forming receptacle as in claim 1, aperture walls defining cross-sectional areas of such apertures along the thickness of said sheet material, including a first locus defining a smallest cross-sectional area, and a second locus defining a relatively larger cross-sectional area displaced from the smallest cross-sectional area and disposed, from the first locus, toward the second major surface of said sheet material.

4. A forming receptacle as in claim 3 wherein the smallest cross-sectional area is displaced from and between both of the first and second surfaces.

5. A forming receptacle as in claim 1, the apertures defining cross-sectional areas proximate the first and second surfaces, the cross-sectional area proximate the second surface being greater than the cross-sectional area proximate the first surface.

6. A forming receptacle as in claim 1 wherein said apertures comprise aperture walls extending generally perpendicular to the first surface, from loci adjacent the first surface, to interior loci between the first surface and the second surface, and tapering generally outwardly from the interior loci to the second major surface, whereby open areas defined by the respective apertures at the second major surface are greater than open areas defined by respective ones of such apertures at the first major surface.

7. A forming receptacle as in claim 1 wherein said aperture walls taper inwardly from the first major surface and toward the second major surface, to a throat zone, and taper outwardly from the throat zone to the second major surface, such that the throat zone defines an opening smaller in cross-sectional area than corresponding openings defined by the respective aperture at either of the first or second major surfaces.

8. A forming receptacle as in claim 2 wherein a respective aperture defines an opening at the first major surface, the opening having an open area corresponding to the area of a circle having a diameter of at least about 0.009 inch, up to about 0.040 inch.

9. A forming receptacle as in claim 2 wherein a respective aperture defines an opening at the first major surface, the opening having an open area corresponding to the area of a circle having a diameter of at least about 0.010 inch, up to about 0.025 inch.

10. A forming receptacle as in claim 2 wherein a respective aperture defines an opening at the first major surface, the opening having an open area corresponding to the area of a circle having a diameter of at least about 0.011 inch, up to about 0.015 inch.

11. A forming receptacle as in claim 2 wherein said matrix of sheet material at the first major surface generally has a minimum projected width between respective ones of the apertures of about 0.003 inch to about 0.015 inch.

12. A forming receptacle as in claim 8 wherein aperture walls of adjacent ones of the apertures intersect the second major surface without intersecting each other and wherein such aperture walls of adjacent first and second ones of the apertures define nominal distances therebetween without intersecting each other.

13. A forming receptacle as in claim 12 wherein said matrix of sheet material at the second major surface generally has a minimum width between respective ones of the apertures of about 0.0007 inch up to about 0.004 inch.

14. A forming receptacle as in claim 1 wherein the array of apertures is arranged in a series of parallel rows of apertures, wherein spacing between apertures in a given row is substantially constant from row to row. and wherein the rows are displaced laterally with respect to each other such that adjacent apertures in adjacent rows define angles of about 50 degrees to about 70 degrees with respect to an imaginary line parallel to the rows.

15. A forming receptacle as in claim 1 wherein the array of apertures is arranged in a series of parallel rows of apertures, wherein spacing between apertures in a given row is constant from row to row, and wherein the rows are displaced laterally with respect to each other such that adjacent apertures in adjacent rows define angles of about 80 degrees to about 90 degrees with respect to an imaginary line parallel to the rows.

16. A forming receptacle as in claim 1 wherein the array of apertures is arranged sporadically, wherein spacing and orientation between apertures in a given row is substantially variable.

17. A forming receptacle as in claim 2 wherein said sheet material defines a bottom wall of said receptacle and a side wall of said receptacle extending upwardly from said bottom wall, wherein said apertures, measured at a smallest cross-section of opening defined by each such aperture, in combination define a composite open area representing at least about 35 percent of the combined areas of said bottom wall and said side wall.

18. A forming receptacle as in claim 17 wherein said bottom wall and said side wall, in conjunction, comprise a particulate receiving cavity having a depth of at least about 0.001 inch to about 2.00 inches.

19. A forming receptacle as in claim 17 wherein said bottom wall and said side wall, in conjunction, comprise a particulate receiving cavity having a depth of about 0.00 inch.

20. A forming receptacle as in claim 1 wherein thickness of said sheet material is about 0.003 inch to about 0.030 inch.

21. A forming receptacle as in claim 1 wherein structures of the apertures reflect photochemical machining.

22. A forming receptacle as in claim 1 wherein the length of said receptacle is about 10 inches to about 30 inches.

23. A forming drum designed and configured to form, in a continuous process, particulate congregates for use as absorbent cores in personal care absorbent articles, said forming drum comprising mounting structure for mounting said forming drum about an axis of rotation, and forming receptacle repositories extending about at least a portion of a circumference of said forming drum and supported from said mounting structure, the forming receptacle repositories including ones of forming receptacles of claim 1 mounted about the circumference of said drum, said forming receptacles being effective to receive and accumulate thereon elongate fibers, and particles of super-absorbent material, thereby to form such congregates.

24. A forming drum designed and configured to form, in a continuous process, particulate congregates for use as absorbent cores in personal care absorbent articles, said forming drum comprising mounting structure for mounting said forming drum about an axis of rotation, and forming receptacle repositories extending about at least a portion of a circumference of said forming drum and supported from said mounting structure, the forming receptacle repositories including ones of forming receptacles of claim 2 mounted about the circumference of said drum, said forming receptacles being effective to receive and accumulate thereon elongate fibers, and particles of super-absorbent material, thereby to form such congregates.

25. A forming drum designed and configured to form, in a continuous process, particulate congregates for use as absorbent cores in personal care absorbent articles, said forming drum comprising mounting structure for mounting said forming drum about an axis of rotation, and a forming receptacle as in claim 1, said forming receptacle being uniform and continuous, and extending about substantially an entire circumference of said forming drum and supported from said mounting structure, said forming receptacle being effective to receive and accumulate thereon elongate fibers, and particles of super-absorbent material, thereby to form such congregates.

26. A forming receptacle adapted and configured to receive particulate material thereon, including super-absorbent particles, for thereby fabricating particulate congregates for use as absorbent cores in personal care absorbent articles, said forming receptacle comprising a substrate which defines a particulate-receiving cavity in said receptacle, said substrate comprising elements defining a first major side disposed toward the cavity, an opposing second major side disposed away from the cavity, and a thickness between the first and second major sides, and an array of apertures extending through at least a portion of said substrate, and connecting said first and second major sides, aperture walls defining cross-sectional areas of such apertures along the thickness of said substrate, including a locus defining a smallest cross-sectional area, and a locus defining a relatively larger cross-sectional area displaced from the smallest cross-sectional area and disposed toward the second major side of said substrate.

27. A forming receptacle as in claim 26 wherein the aperture walls extend from the first major side to the second major side, and wherein respective said aperture walls taper generally outwardly between the first major side and the second major side.

28. A forming receptacle as in claim 26, the aperture walls defining cross-sectional areas of such apertures along the thickness of said substrate, including a first locus defining a smallest cross-sectional area, and a second locus defining a relatively larger cross-sectional area displaced from the smallest cross-sectional area and disposed, from the first locus, toward the second major side of said substrate.

29. A forming receptacle as in claim 28 wherein the smallest cross-sectional area is displaced from and between both of the first and second sides.

30. A forming receptacle as in claim 26, said aperture walls defining cross-sectional areas proximate the first and second sides, the cross-sectional area of a given aperture, proximate the second side, being greater than the cross-sectional area proximate the first side.

31. A forming receptacle as in claim 26 wherein said aperture walls extend generally perpendicular to the first side, from loci adjacent the first side, to interior loci between the first side and the second side, and taper generally outwardly from the interior loci to the second major side, whereby open areas defined by the respective apertures at the second major side are greater than open areas defined by respective ones of such apertures at the first major side.

32. A forming receptacle as in claim 26 wherein said aperture walls taper inwardly from the first major side and toward the second major side, to a throat zone, and taper outwardly from the throat zone to the second major side, such that the throat zone defines an opening smaller in cross-sectional area than corresponding openings defined by the respective aperture at either of the first or second major sides.

33. A forming receptacle as in claim 27 wherein a respective aperture defines an open area at the first major side corresponding to the area of a circle having a diameter of at least about 0.009 inch, up to about 0.040 inch.

34. A forming receptacle as in claim 27 further comprising a matrix of said substrate between respective ones of the apertures and defining outer perimeters of respective ones of the apertures, wherein matrix of substrate at the first major side generally has a minimum projected width between respective ones of the apertures of about 0.003 inch to about 0.015 inch.

35. A forming receptacle as in claim 33 wherein aperture walls of adjacent ones of the apertures intersect the second major side without intersecting each other and wherein such aperture walls of adjacent first and second ones of the apertures define a nominal distance therebetween without intersecting each other.

36. A forming receptacle as in claim 35 further comprising a matrix of said substrate between respective ones of the apertures and defining outer perimeters of respective ones of the apertures, wherein said matrix of substrate at the second major side generally has a minimum width between respective ones of the apertures of about 0.0007 inch, up to about 0.004 inch.

37. A forming receptacle as in claim 26 wherein the array of apertures is arranged in a series of parallel rows of apertures, wherein spacing between apertures in a given row is substantially constant from row to row, and wherein the rows are displaced laterally with respect to each other such that adjacent apertures in adjacent rows define angles of about 50 degrees to about 90 degrees with respect to an imaginary line parallel to the rows.

38. A forming receptacle as in claim 27 wherein said substrate defines a bottom wall of said receptacle and a side wall of said receptacle extending upwardly from said bottom wall, wherein said apertures, measured at a smallest cross-section of opening defined by each such aperture, in combination define a composite open area representing at least about 35 percent of the combined areas of said bottom wall and said side wall.

39. A forming receptacle as in claim 27 wherein thickness of said substrate is about 0.003 inch to about 0.030 inch.

40. A forming receptacle as in claim 26 wherein structures of the apertures reflect photochemical machining.

41. A forming drum designed and configured to form, in a continuous process, particulate congregates for use as absorbent cores in personal care absorbent articles, said forming drum comprising mounting structure for mounting said forming drum about an axis of rotation, and forming receptacle repositories extending about a circumference of said forming drum and supported from said mounting structure, the forming receptacle repositories including ones of forming receptacles of claim 26 mounted about the circumference of said drum, said forming receptacles being effective to receive and accumulate thereon elongate fibers, and particles of super-absorbent material, thereby to form such congregates.

42. A method for forming a congregate of particulate material for use as an absorbent core in an absorbent article, wherein the particulate material comprises particles of super-absorbent material, the method comprising:

(a) conveying the particulate material in a gaseous carrier toward a forming receptacle, the forming receptacle comprising sheet material defining a particulate-receiving cavity in the receptacle, the sheet material having a first major surface disposed toward the cavity, an opposing second major surface disposed away from the cavity, a thickness between the first and second major surfaces, and an array of apertures extending through at least a portion of the sheet material and defining passage ways between the first and second major surfaces, the passage ways being defined by aperture walls which taper generally outwardly from central axes of the respective passage ways, and from proximate the first major surface toward the second major surface, whereby the passage ways tend to generally progressively expand in cross-sectional area as one progresses toward the second major surface, and wherein projected areas of the particles of the super-absorbent material are generally larger than projected areas of the apertures; and (b) receiving and collecting particles of the particulate material in the cavity and thereby forming the congregate while generally not conveying particles of the super-absorbent material into the passage ways, and whereby undersize particles of super-absorbent material which do enter respective ones of the passage ways tend to pass entirely through the passage ways and not become lodged in such passage ways because of being released to pass through such passage ways, by the generally progressively expanding cross-sections of such passage ways along the direction of travel of such particles.

43. A method as in claim 42, the method comprising receiving and collecting the particles on a such forming receptacle wherein the projected area of a respective such aperture is defined by a relatively more constrictive throat zone of the respective passage way, the throat zone being disposed closer to the first major surface than to the second major surface.

44. A method as in claim 43, the method comprising receiving and collecting the particles on a such forming receptacle wherein a projection of the throat zone is no more than 25 percent smaller in cross-sectional area than a projection of the respective aperture at the first surface.

45. A method as in claim 43, the method comprising receiving and collecting the particles on a such forming receptacle wherein a projection of the throat zone is no more than 15 percent smaller in cross-sectional area than a projection of the respective aperture at the first surface.

46. A method as in claim 43, the method comprising receiving and collecting the particles on a such forming receptacle wherein a projection of the throat zone is substantially the same size in cross-sectional area as a projection of the respective aperture at the first surface.

47. A method as in claim 42, the method comprising receiving and collecting the particles on a such forming receptacle wherein a respective aperture defines an opening at the first major surface, the opening having an open area corresponding to the area of a circle having a diameter of at least about 0.009 inch and 0.040 inch.

48. A method as in claim 42, the method comprising receiving and collecting the particles on a such forming receptacle wherein the matrix of sheet material generally defines a minimum projected width between respective ones of the apertures of about 0.003 inch to about 0.015 inch.

49. A method as in claim 42, the method comprising receiving and collecting the particles on a such forming receptacle wherein aperture walls of adjacent ones of the apertures intersect the second major surface without intersecting each other and wherein such aperture walls of adjacent first and second ones of the apertures define a nominal distance therebetween without intersecting each other.

50. A method as in claim 42, the method comprising receiving and collecting the particles on a such forming receptacle wherein the array of apertures is arranged in a series of parallel rows of apertures, wherein spacing between apertures in a given row is substantially constant from row to row, and wherein the rows are displaced laterally with respect to each other such that adjacent apertures in adjacent rows define angles of about 50 degrees to about 90 degrees with respect to an imaginary line parallel to the rows.

51. A method as in claim 42, the method comprising receiving and collecting the particles on a such forming receptacle wherein the apertures, measured at a smallest cross-section of opening defined by each such aperture, in combination define a composite open area representing at least about 35 percent of the combined areas of the bottom wall and the side wall.

52. A method as in claim 42, the method comprising receiving and collecting the particles on a such forming receptacle wherein the super-absorbent material is generally spherically-shaped.

53. A method as in claim 42, the method comprising receiving and collecting the particles on a such forming receptacle wherein the particles of super-absorbent material are generally oblong-shaped, having a length-to-width ratio of no more than 4/1.

* * * * *